United States Patent
Blomqvist et al.

(10) Patent No.: US 9,277,886 B2
(45) Date of Patent: *Mar. 8, 2016

(54) METHOD, IMPLANTABLE MEDICAL DEVICE, AND SYSTEM FOR DETERMINING THE CONDITION OF A HEART VALVE

(71) Applicant: ST. JUDE MEDICAL AB, Jarfalla (SE)

(72) Inventors: Andreas Blomqvist, Taby (SE); Karin Jarverud, Solna (SE)

(73) Assignee: ST. JUDE MEDICAL AB, Jarfalla (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/798,174

(22) Filed: Jul. 13, 2015

(65) Prior Publication Data
US 2015/0313544 A1    Nov. 5, 2015

Related U.S. Application Data

(62) Division of application No. 13/131,527, filed as application No. PCT/SE2008/000670 on Nov. 28, 2008, now Pat. No. 9,108,064.

(51) Int. Cl.
| | |
|---|---|
| *A61B 5/00* | (2006.01) |
| *A61B 5/02* | (2006.01) |
| *A61B 5/04* | (2006.01) |
| *A61B 5/042* | (2006.01) |
| *A61B 5/0432* | (2006.01) |
| *A61N 1/362* | (2006.01) |
| *A61N 1/365* | (2006.01) |
| *A61N 1/368* | (2006.01) |
| *A61N 1/37* | (2006.01) |

(52) U.S. Cl.
CPC ............. *A61B 5/686* (2013.01); *A61B 5/02028* (2013.01); *A61B 5/042* (2013.01); *A61B 5/04012* (2013.01); *A61B 5/0432* (2013.01); *A61N 1/368* (2013.01); *A61N 1/3627* (2013.01); *A61N 1/36521* (2013.01); *A61N 1/3702* (2013.01); *A61N 1/3682* (2013.01); *A61N 1/3684* (2013.01)

(58) Field of Classification Search
CPC .. A61B 5/0452; A61B 5/0006; A61B 5/0002; A61B 5/0428; A61N 1/3962; A61N 1/368; A61N 1/3627
USPC .............................. 607/4, 9, 17; 600/508, 515
See application file for complete search history.

(56) References Cited

U.S. PATENT DOCUMENTS

| | | |
|---|---|---|
| 5,427,112 A | 6/1995 | Noren et al. |
| 5,556,419 A | 9/1996 | Jarverud et al. |
| 5,792,194 A | 8/1998 | Morra |

(Continued)

OTHER PUBLICATIONS

Restriction Requirement, mailed Jul. 3, 202014—Parent U.S. Appl. No. 13/131,527.

(Continued)

*Primary Examiner* — Theodore Stigell
*Assistant Examiner* — Roland Dinga

(57) ABSTRACT

An implantable medical device has an impedance processor that determines impedance data reflective of the transvalvular impedance of a heart valve of a heart during a heart cycle. The determined impedance data are processed by a representation processor that estimates diastolic and systolic transvalvular impedance representations. A condition processor determines the presence of any heart valve malfunction, such as valve regurgitation and/or stenosis, of the heart valve based on the estimated diastolic and systolic transvalvular impedance representations.

10 Claims, 11 Drawing Sheets

(56) References Cited

U.S. PATENT DOCUMENTS

| | | |
|---|---|---|
| 7,010,347 B2 | 3/2006 | Schecter |
| 7,410,467 B2 | 8/2008 | Cooper |
| 2001/0021864 A1 | 9/2001 | Molin |
| 2004/0127944 A1 | 7/2004 | Casset |
| 2004/0147968 A1 | 7/2004 | Casset |
| 2006/0173502 A1 | 8/2006 | Bayham |
| 2007/0123943 A1 | 5/2007 | Patangay |
| 2007/0191901 A1* | 8/2007 | Schecter .............. A61N 1/3627 607/17 |
| 2010/0121398 A1 | 5/2010 | Bjorling et al. |

OTHER PUBLICATIONS

NonFinal Office Action, mailed Dec. 5, 2014—Parent U.S. Appl. No. 13/131,527.

Notice of Allowance, mailed May 22, 2015—Parent U.S. Appl. No. 13/131,527.

Di Gregorio, F. et al., "Transvalvular Impedance (TVI) Recording Under Electrical and Pharmacological Cardiac Stimulation," PACE. 1996;19:1689-1693.

Arthur, Wayne et al., "Measurement of Impedance to Assess Myocardial Contractility and Rhythm Stability," Physiol. Meas. 2000;24:R43-R54.

\* cited by examiner

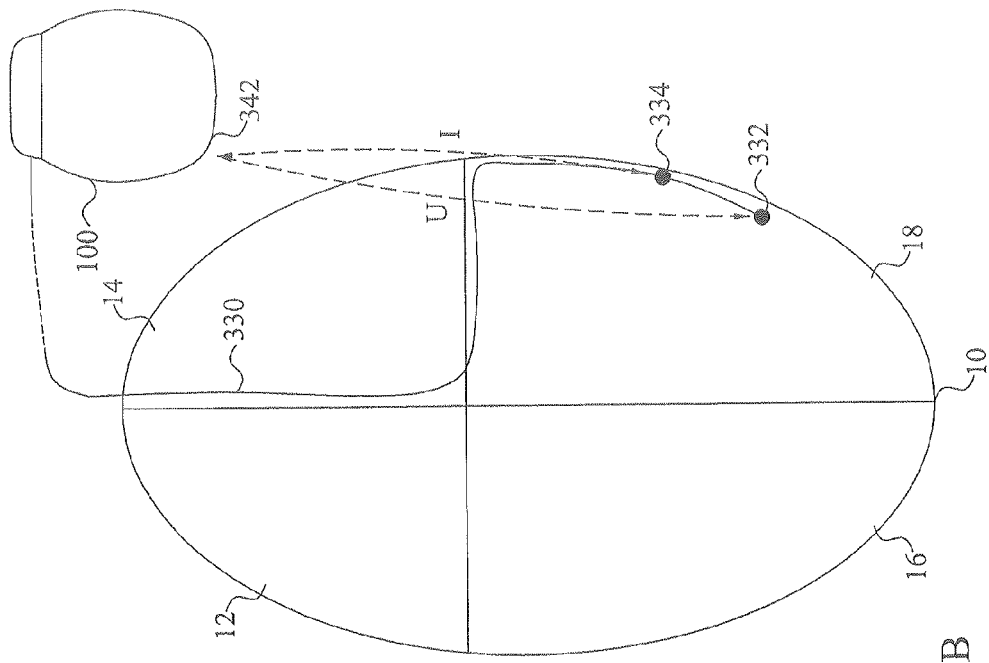
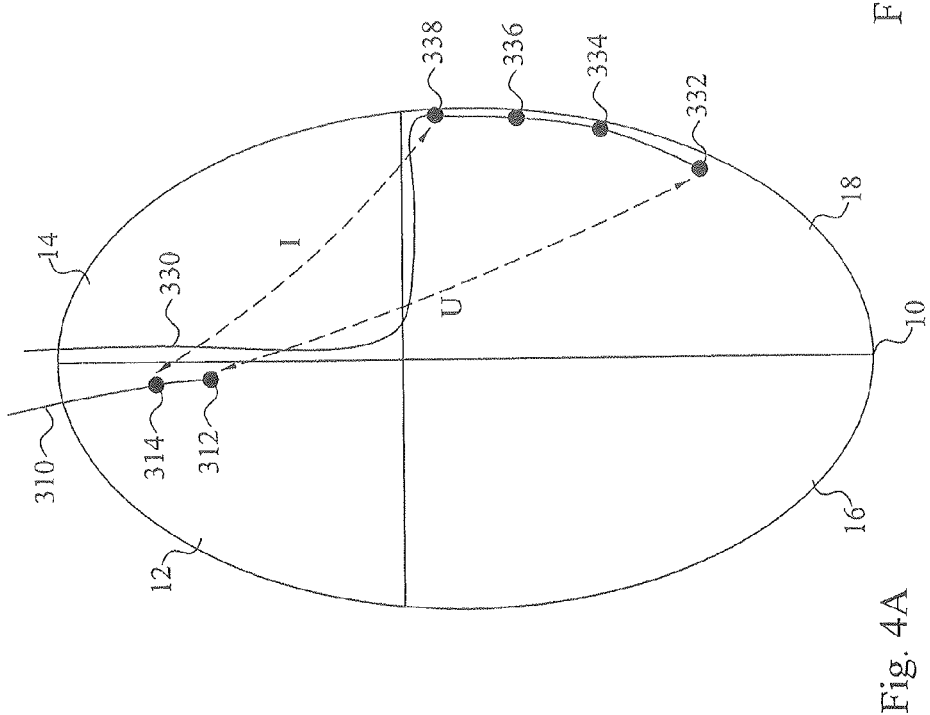
Fig. 4A
Fig. 4B

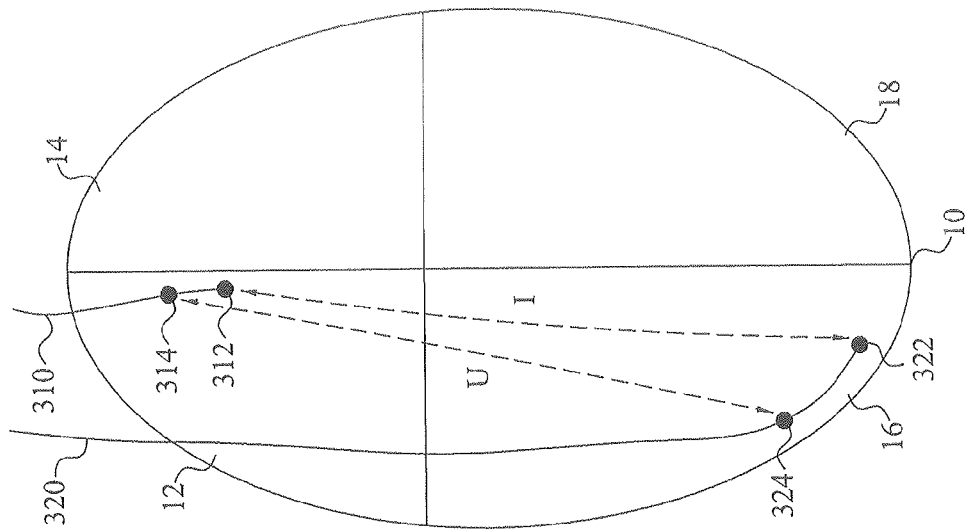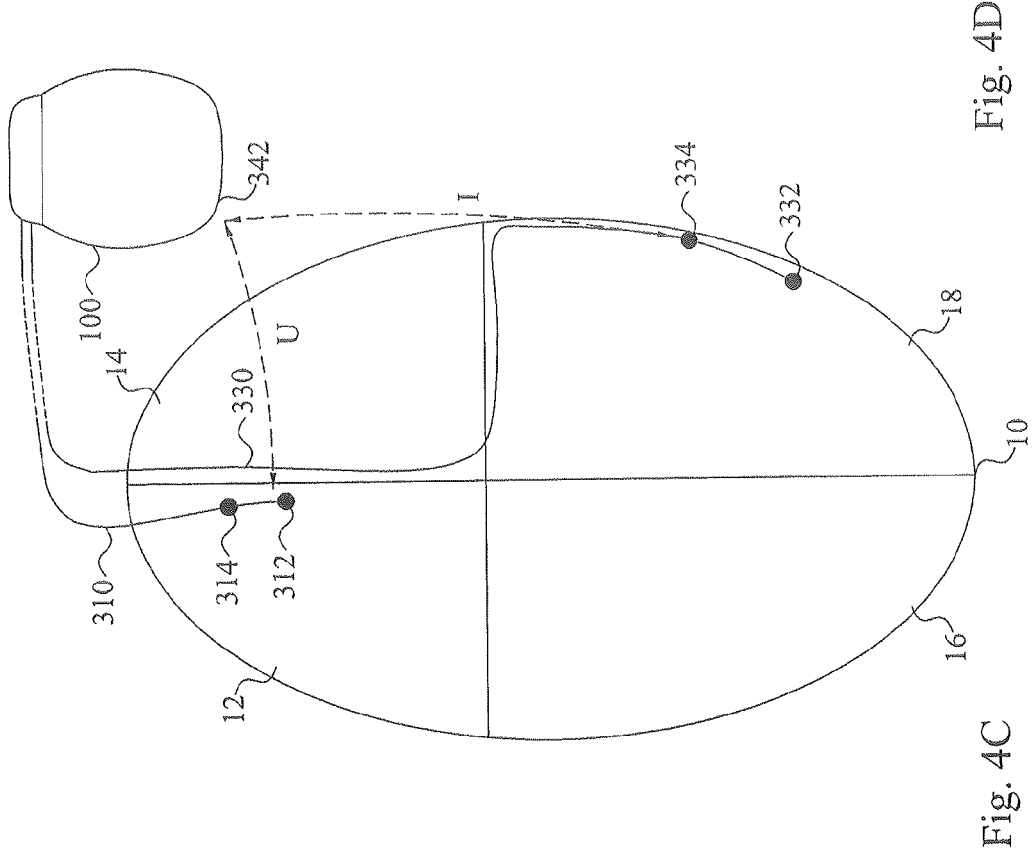

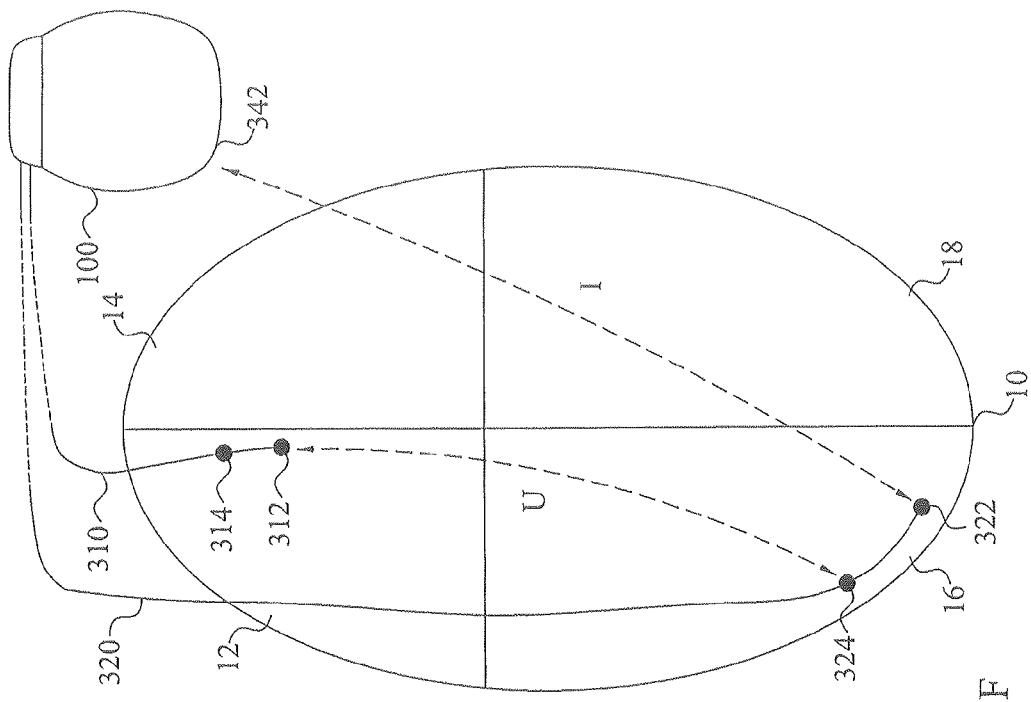
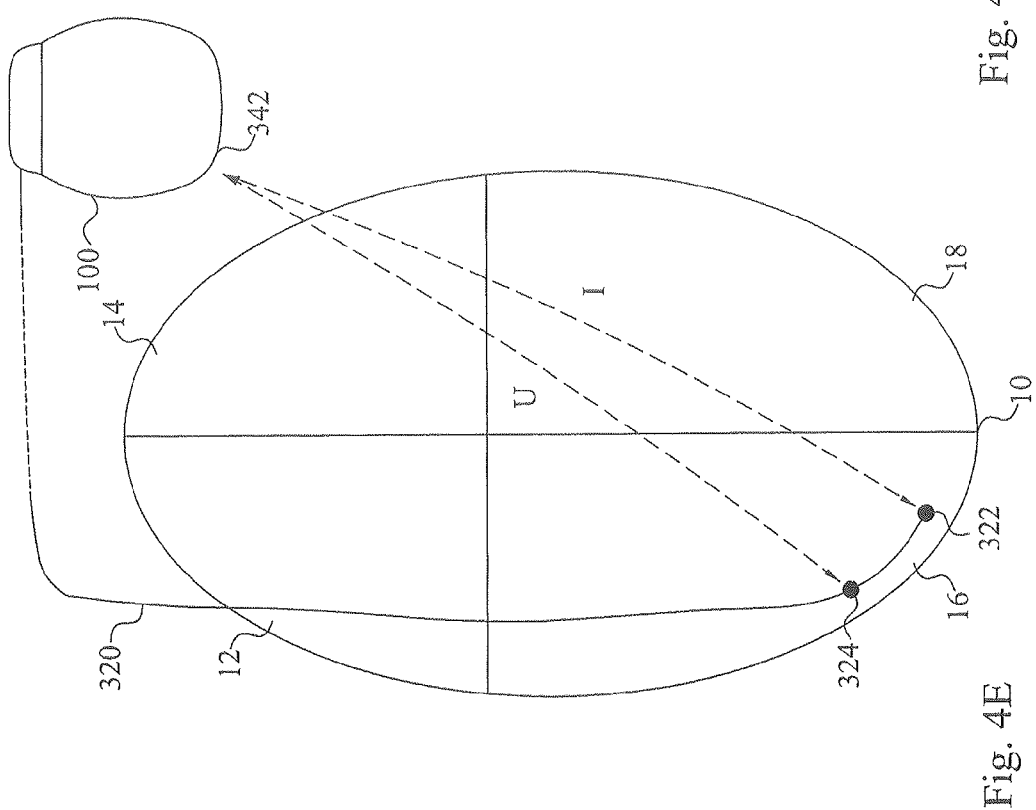

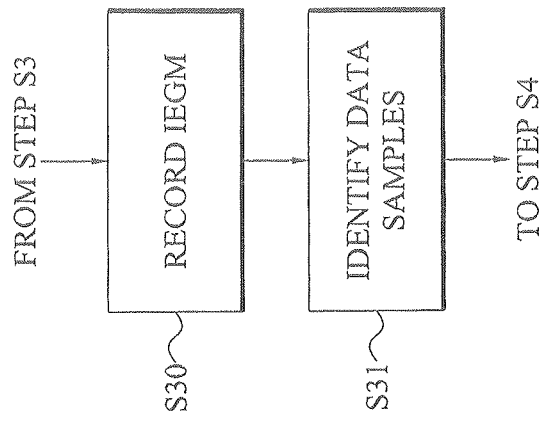
Fig. 12
Fig. 11
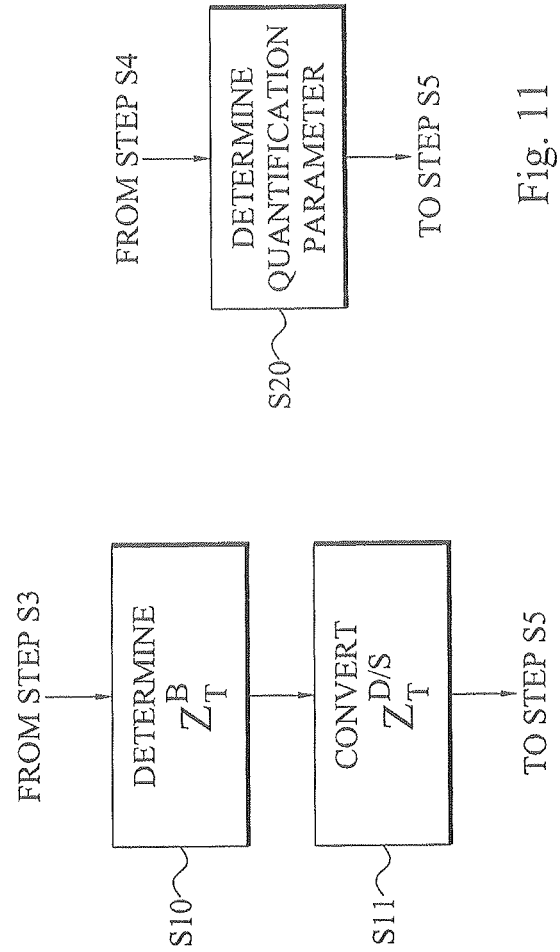
Fig. 10

METHOD, IMPLANTABLE MEDICAL DEVICE, AND SYSTEM FOR DETERMINING THE CONDITION OF A HEART VALVE

CROSS REFERENCE TO RELATED APPLICATIONS

This a division of U.S. patent application Ser. No. 13/131, 527, filed May 5, 2011, which is a 371 Application of International Application PCT/SE2008/00670, filed Nov. 28, 2008.

FIELD OF THE INVENTION

The present invention generally relates to valve condition determination, and in particular to devices and methods for determining and monitoring the condition and operation of heart valves.

BACKGROUND OF THE INVENTION

The human heart comprises four heart valves controlling the flow of blood from the atriums to the ventricles and from the ventricles further on into the pulmonary or systemic circulation system. The operation of the heart valves is critical for the well-being of the subject and any valve malfunctions may lead to severe and possibly life-threatening conditions.

Generally, blood flowing incorrectly backwards through a heart valve, i.e. regurgitation, is either a primary valve related problem that might cause acute heart failure or is a secondary problem in heart failure patients. If it is a primary valve related problem, i.e. the valve has ruptured or has been damaged, e.g. through infection, valve surgery is typically employed, where the damaged valve is repaired or replaced with a new artificial valve. Any heart failure will then often resolve automatically once the valve function has been restored.

If it is a secondary problem in heart failure patients, the main source for regurgitation is probably caused by the dilated state of the heart, making it difficult for the valve to close tightly. In this latter case, monitoring valve condition and status may serve as a valuable tool to monitor heart failure.

Another common heart valve problem is valve stenosis, where the valve kinetics are disturbed making it difficult to close properly or open sufficiently.

There is therefore a need for a tool of monitoring heart valve function in order to detect any deleterious heart valve effects and/or detect primary medical conditions manifesting in change in heart valve operation.

US 2007/0191901 discloses a cardiac resynchronization therapy (CRT) device that is being programmed based on various impedance-related parameters. Multi-vector impedance signals associated with dynamic intracardiac impedance are acquired and related to specific time frames of the cardiac cycle to derive indices representative of systolic and diastolic cardiac performance. The impedance signals are further adjusted by static impedance signals associated with pulmonary impedance as to derive composite indices representative of cardiac performance and pulmonary vascular congestion.

US 2007/0191901 also discusses that aortic valve stenosis can be detected using an aortic valve function:

$$f = \frac{1}{T_{AVO} - \frac{T_Z}{\frac{dZ}{dt}}}$$

where $T_{AVO}$ denotes the time of aortic valve opening, $T_Z$ denotes the onset time of positive impedance slope and $$\frac{dZ}{dt}$$

is the first derivative of the impedance signal and is included to account for cardiac output. A similar equation can be used for assessment of aortic valve regurgitation using delays in time to aortic valve closure from the onset of aortic valve opening or from time of peak impedance.

SUMMARY OF THE INVENTION

The prior art technique disclosed in US 2007/0191901 requires the identification of the opening and closing time of the aortic valve. These exact times may be difficult to identify in the impedance data, thereby needing additional sensor equipment, such as recording of echocardiograms, in order to identify the required times. The embodiments of the present invention overcome this and other problems with the prior art technique.

It is a general object of the invention to provide a determination of heart valve conditions.

It is another object of the invention to provide an implantable medical device capable of monitoring and determining heart valve conditions in a subject.

The above objects are achieved in accordance with the present invention by an implantable medical device that is connectable to multiple electrodes that are implantable for applying and applying electric signals from at least a portion of a heart. An electric signal is applied, using the electrodes, over at least a portion of the heart and a resulting electric signal is collected from the heart using the electrodes. The electric signals are processed by an impedance processor for determining impedance data reflective of the transvalvular impedance of a heart valve that is being monitored. The impedance data are descriptive (representative) of the impedance over the valve and the valve plane during at least one heart cycle to thereby contain transvalvular impedance data samples during both diastole and systole of the at least one heart cycle.

A representation processor is implemented for estimating a diastolic transvalvular impedance representation and a systolic transvalvular impedance representation for the monitored heart valve. The implantable medical device has a condition processor that determines a condition of the heart valve based on the estimated diastolic and systolic transvalvular impedance representations. The condition processor concludes that the heart valve is operating correctly, i.e. normal condition, or determines the presence of a valve malfunction, such as valve regurgitation or stenosis, based on the transvalvular impedance representations.

Depending on implantation site of the electrodes used for signal application and/or signal collection, the implantable medical device can monitor the condition of one or more heart valves in the heart. The implantable medical device may therefore potentially determine the presence of:

mitral/tricuspid valve stenosis—significant change, i.e. increase, in diastolic transvalvular impedance but no significant change in systolic transvalvular impedance;

mitral/tricuspid valve regurgitation—significant change, i.e. decrease, in systolic transvalvular impedance but no significant change in diastolic transvalvular impedance;

aortic/pulmonary valve stenosis—significant change, i.e. increase, in systolic transvalvular impedance but no significant change in diastolic transvalvular impedance; and aortic/pulmonary valve regurgitation—significant change, i.e. decrease, in diastolic transvalvular impedance but no significant change in systolic transvalvular impedance.

Embodiments offer the following advantages:

Allows heart valve condition determination and monitoring without the usage of any extra, dedicated sensor equipment; and Can be used for monitoring any of the four heart valves or a combination of at least two heart valves.

Other advantages offered by the embodiments will be appreciated upon reading of the below description of the embodiments.

BRIEF DESCRIPTION OF THE DRAWINGS

FIG. 3 is a schematic block diagram illustrating an embodiment of the representation processor of the implantable medical device in FIG. 2.

FIGS. 4A-4F illustrate lead configurations that can be used for determining transvalvular impedances according to different embodiments.

FIG. 10 is a flow diagram illustrating an embodiment of the estimating step of the determining method in FIG. 9.

FIG. 11 is a flow diagram illustrating an additional, optional step of the determining method in FIG. 9.

FIG. 12 is a flow diagram illustrating additional, optional steps of the determining method in FIG. 9.

DESCRIPTION OF THE PREFERRED EMBODIMENTS

Figure 1:
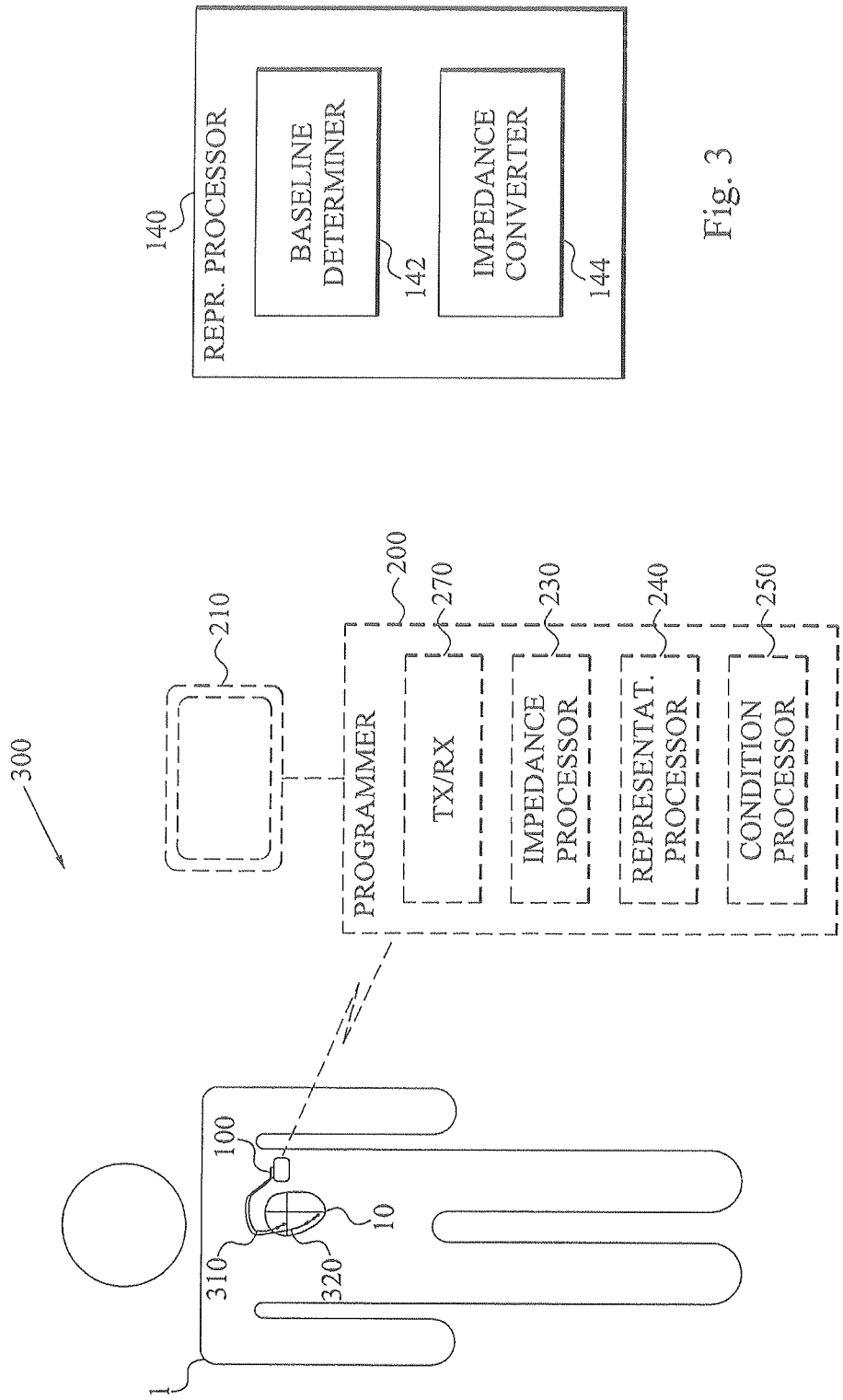
FIG. 1 is a schematic overview of a human subject having an implantable medical device according to an embodiment and an indicated external communication device.

Throughout the drawings, the same reference characters will be used for corresponding or similar elements.

The embodiments generally relate to devices and methods for monitoring and determining the condition of a heart valve of a heart in an animal subject, preferably mammalian subject and more preferably a human subject.

Figure 8:
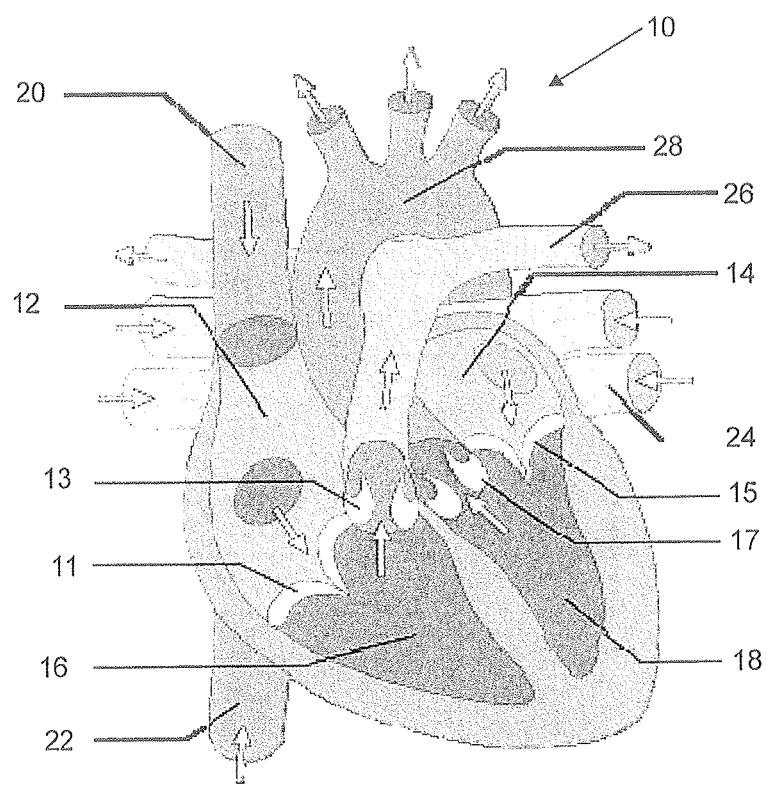
FIG. 8 is a schematic illustration of a heart with connecting main arteries and veins.

As is illustrated in FIG. 8, the human heart 10 has four heart valves 11, 13, 15, 17. Blood from the systemic circulation system enters the right atrium 12 by the superior vena cava 20 and the interior vena cava 22. The blood flows from the right atrium 12 through a first valve, the tricuspid valve 11, into the right ventricle 16. The oxygen depleted blood is pumped by the contractile action of the right ventricle through the pulmonary valve 13 to the lungs via the pulmonary artery 26.

Correspondingly, on the left side of the heart 10 blood enters the left atrium 14 from the pulmonary vein 24. The blood flows from the left atrium 14 through the mitral valve 15, also denoted bicuspid valve, to the left ventricle 16. The oxygen rich blood leaves the left ventricle through the aortic valve 17 and enters the aorta 28.

The operation of these four heart valves 11, 13, 15, 17 is critical for the efficient pumping of the blood through the pulmonary and systemic circulation systems and the well-being of the subject. Medical conditions and malfunctions can effect these valves 11, 13, 15, 17 and thereby the operation of the heart 10 as whole.

For instance, medical conditions can cause a leakage of blood backwards through a heart valve, i.e. regurgitation. Valve regurgitation may in turn be due to a primary valve problem, such as a valve rupture, which may occur due to a localized heart infarct in the area around the muscle anchoring the chordae tendineae attached to the valves, or a valve damage through an infection. Also secondary problems, such as a dilation of the heart in heart failure patients, may negatively affect the valves leading to regurgitation.

Another type of medical condition that can affect the valves is stenosis. In stenosis the valves become stiffer and its kinetics is disturbed causing them not to open sufficiently.

The present invention is an efficient technique for monitoring the operation of the heart valves and determining whether a negative medical condition has occurred to a valve or if there is a worsening of a previously determined medical condition. The valve condition monitoring and determination can furthermore be conducted by an implantable medical device (IMD) having cardiac leads but does not require any dedicated heart valve sensors or other equipment. In clear contrast, conventional cardiac leads having electrodes attached to or positioned close to the heart can be used for generating data that is processed by the IMD for the purpose of the valve condition monitoring and determination.

As is further described herein, embodiments can be used for monitoring and determining the condition of one of the four heart valves. Alternatively, multiple heart valves and potentially all four valves can be monitored depending on the number of electrodes used and their implantation sites.

FIG. 1 is a schematic overview of a human patient 1 having an IMD 100 as taught herein. In the figure, the IMD 100 is illustrated as a device that monitors and/or provides therapy to the heart 10 of the patient 1, such as a pacemaker, cardiac defibrillator or cardioverter. The IMD 100 is, in operation, connected to one or more, two in the figure, cardiac leads 310, 320 inserted into different heart chambers, the right atrium and the right ventricle in the figure. The present invention is though not limited to right chamber leads 310, 320 but can also be used in connection with leads positioned in the left atrium or ventricle of the heart 10. Actually, also non-intracardiac leads, including epicardial leads can also be used. The IMD 100 must further not necessarily be connected to two cardiac leads 310, 320 but could alternatively be connected to a single lead 320 carrying at least one electrode or more than two cardiac leads 310, 320.

The patient 1 illustrated in FIG. 1 is a human patient 1. However, the present invention is not limited thereto, but can also be applied to IMDs 100 implanted in other animals, in particular other mammals.

FIG. 1 also illustrates an external programmer or clinician's workstation 200 that can communicate with the IMD 100. As is well known in the art, such a programmer 200 can be employed for transmitting IMD programming commands, using an included transmitter 270, causing a reprogramming of different operation parameters and modes of the IMD 100. Furthermore, the IMD 100 can upload diagnostic data descriptive of different medical parameters or device operation parameters collected by the IMD 100 to a receiver 270 of the programmer 200. Such uploaded data may optionally be further processed in the programmer 200 before display to a clinician on a connected display screen 210. In the light of the present disclosure, such uploaded data can include the valve condition information determined according to embodiments and other data relating to heart valve conditions.

Figure 2:
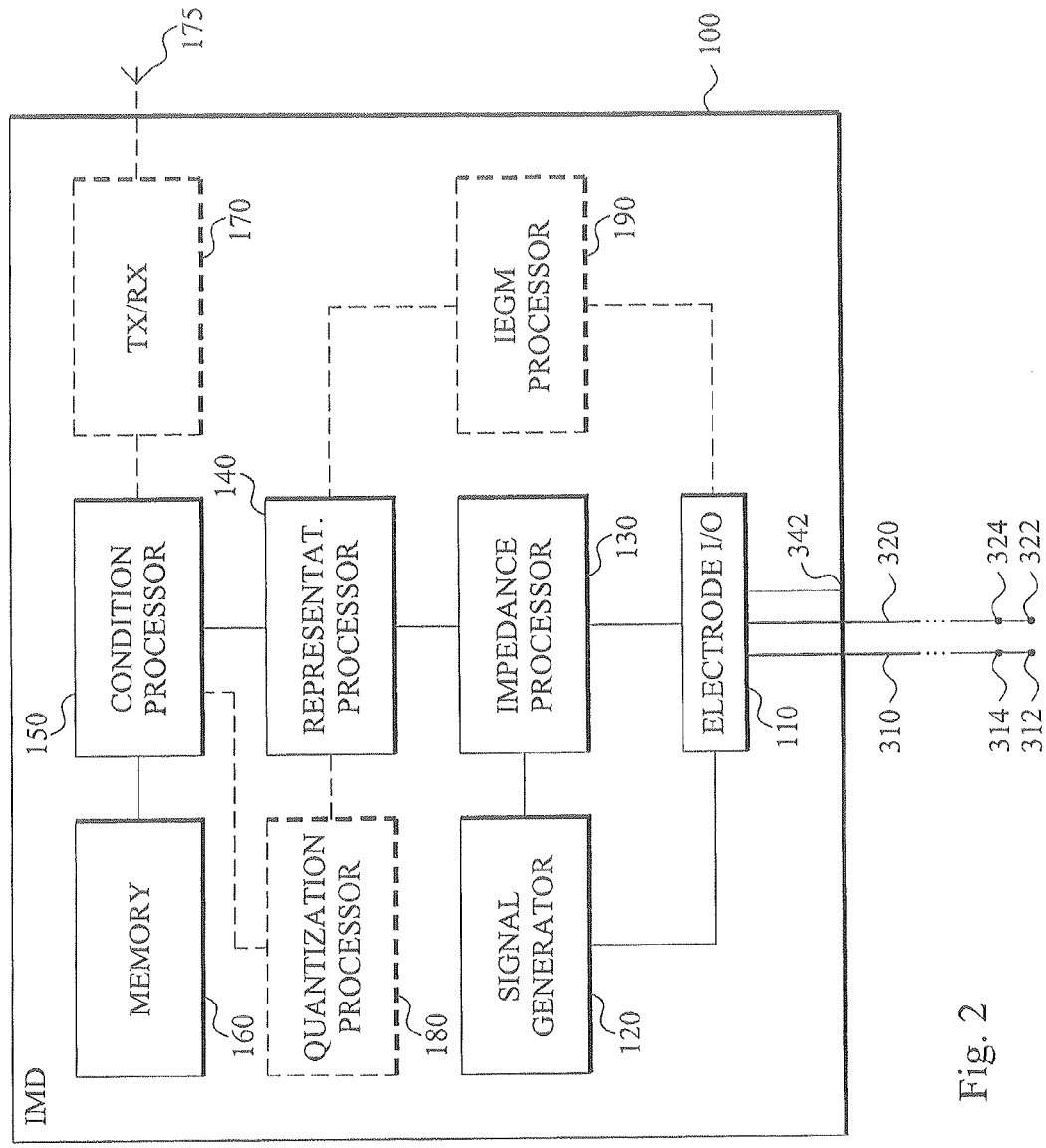
FIG. 2 is a schematic block diagram of an embodiment of an implantable medical device.

FIG. 2 is a schematic block diagram of an IMD 100 according to an embodiment. The IMD 100 comprises an electrode connecting arrangement 110 represented by an electrode input/output (I/O) 110 in the figure.

This electrode I/O 110 is, in operation, connectable to multiple electrodes 312, 314, 322, 324, 342 of which at least one is designed for being implanted in or at least in connection with the heart. As a consequence, at least one of the multiple electrodes 312, 314, 322, 324, 342 is arranged on a cardiac lead 310, 320 connectable to the electrode I/O 110. This further implies that at least one but not all of the multiple electrodes 312, 314, 322, 324, 342 may not necessarily be lead-arranged or be implanted in the immediate vicinity of the heart. An example of such an electrode 342, is an electrode 342 constituting the whole or a portion of the case or can of the IMD 100.

As is well known in the art, an implantable lead or catheter 310, 320 has a proximal end connectable to the IMD 100 through the electrode I/O 110. This IMD-connecting end presents one or more electric terminals that are in electric connection with the electrodes 312, 314, 322, 324 present on the opposite distal lead end, where the electric connection is achieved by electric conductors running along the length of the lead body. The distal lead end with its electrodes 312, 314, 322, 324 is then provided in connection with the heart tissue. For this purpose, the lead 310, 320 can include a tissue anchoring element, such as a helical fixation element, though other fixation elements, such as passive fixation elements, including fines, tines, etc., are also common. The fixation element can indeed constitute one of the electrodes of the lead 310, 320, while remaining electrodes can be ring electrodes often denoted indifferent electrodes in the art, defibrillation electrode, or the like.

The IMD 100 is connected to at least one implantable cardiac lead 310, 320. The cardiac lead 310, 320 can be an intracardiac lead positioned in any of the chambers of the heart, such as right and/or left atrium and/or ventricle. Alternatively, the lead 310, 320 could be epicardially positioned relative the heart, such as in the coronary vein. In the case of multiple connectable leads 310, 320 the IMD 100 can be connected to multiple intracardiac or endocardial leads, multiple epicardial leads or a combination of intracardiac and epicardial leads. In a preferred embodiment, the IMD 100 and the electrode I/O 110 are connected to a ventricular lead 310, such as right ventricular lead and/or coronary vein lead (left ventricular lead), and an atrial lead 320, such a right atrial lead and/or a left atrial lead.

A signal generator 120 of the IMD 100 is electrically connected to the electrode I/O 110 and connectable electrodes 312, 314, 322, 334, 342. The generator 120 generates an electric signal. The electric signal is an alternating current (AC) signal having particular frequencies. The electric signal is applicable over at least a portion of a heart in a subject by two electrodes 312, 322 of the multiple connectable electrodes 312, 314, 322, 324, 342.

In operation, the signal generator 120 generates the electric signal having a defined time-dependent voltage/current profile and forwards the signal to the electrode I/O 110. The electrode I/O 110 directs the electric signal to the two relevant signal applying electrodes 312, 322 to apply the signal over the relevant portion of the heart. As is further described herein, this portion of the heart preferably encompasses the heart valve to be monitored by the IMD 100. If multiple heart valves are to be monitored, the signal generator 120 preferably generates a respective electric signal for each of the heart valves. These electric signals may be the same, i.e. having the same voltage/current profiles and frequencies, or they may be different electric signals. A first such electric signal is then applied over a first pair of connected electrodes 312, 342, whereas at least one second electric signal is applied over a different portion of the heart, typically using a different pair of connected electrodes 322, 342. The at least two electric signals are applied by the respective electrode pairs to the heart, either in parallel or preferably, in order to reduce any interference therebetween, sequentially.

Two electrodes 314, 324 of the multiple connected electrodes 312, 314, 322, 324, 342 collect a resulting electric signal, i.e. resulting AC signal, originating from at least the portion of the heart. This resulting signal is due to the applied electric signal from the signal generator 120. In the case multiple electric signals where generated by the signal generator 120 and applied over different portions of the heart, a respective resulting electric signal is preferably collected by respective electrode pairs for each of the applied electric signals. Thus, for each monitored heart valve a pair of an applied electric signal and a collected resulting signal is available for the IMD 100. In a preferred implementation, the collected resulting electric signal or signals are sensed AC signals.

An impedance processor 130 is electrically connected to the signal generator 120 and the electrode I/O 110. The impedance processor 130 processes the electric signal generated by the signal generator 120 and the resulting electric signal collected by the two electrodes 314, 324 connected to the electrode I/O 110. In more detail, the processor 130 calculates impedance data or signal based on the generated electric signal, such as based on the current of the electric signal, and the resulting electric signals, e.g. based on the measured voltage of the resulting electric signal. This impedance data is reflective of a transvalvular impedance of a monitored heart valve during at least one heart cycle.

In the case multiple heart valves are monitored, the impedance processor 130 also processes the other applied electric signals from the signal generator 120 and the other resulting electric signals collected from the heart. The impedance processor 130 uses these other electric signals for determining respective impedance data or signal reflective of the transvalvular impedance of the monitored heart valves during at least one heart cycle.

Determination of impedance data based on applied and measured electric signals is well-known in the art and is therefore not further described herein.

The impedance processor 130 can utilize different filter combinations, such as bandpass filters, in order to obtain the desired impedance data based on the measured voltage of the resulting electric signal and the current of the applied electric signal. The impedance data determined by the impedance processor 130 can be a complex impedance signal, i.e. comprising a resistive and a reactive component or alternatively an impedance amplitude and phase angle. Alternatively, only the resistive or reactive component or the impedance amplitude is used as impedance data.

In a particular embodiment, the impedance processor 130 can determine the impedance data as average impedance data. In such a case, the electric signal is applied over the relevant heart portion over multiple, preferably consecutive, heart cycles. The resulting electric signal is furthermore measured during multiple heart cycles. The impedance data is then the average impedance during the heart cycle, i.e. including both impedance data determined for diastole and impedance data determined for systole of the heart cycle.

A representation processor 140 is implemented in the IMD 100 connected to the impedance processor 130. The representation processor 140 receives the impedance data from the processor 130 or fetches it from a memory 160 included in the IMD 100 in the case the impedance processor 130 has previously stored the data therein. The impedance processor 140 estimates a diastolic transvalvular impedance representation and a systolic transvalvular impedance representation based on the impedance data. The diastolic transvalvular impedance representation is representative of the transvalvular impedance of the monitored heart valve during diastole, while the systolic transvalvular impedance representation is indicative of the transvalvular impedance originating from the heart valve but during systole of the heart cycle or an average heart cycle.

The determined transvalvular impedance representations are forwarded to a condition processor 150 implemented in the IMD 100. The condition processor 150 uses the diastolic and systolic transvalvular impedance representations for determining a condition of a monitored heart valve.

The IMD 100 preferably has access to respective reference diastolic and systolic transvalvular impedance representations, such as from the memory 160. In such a case, the condition processor 150 compares the diastolic transvalvular impedance representation with the reference diastolic transvalvular impedance representation and compares the systolic transvalvular impedance representation with the reference systolic transvalvular impedance representations.

The condition processor 150 also determines the valve condition, such as normal valve operation or valve malfunction, such as valve regurgitation or valve stenosis, if there is a significant difference between a reference transvalvular impedance representation and the relevant transvalvular impedance representations. A significant difference is present if the diastolic and/or systolic transvalvular impedance representation differs from the reference diastolic and/or systolic transvalvular impedance representation with more than a diastolic/systolic threshold value. If no significant differences are detected the condition processor 150 determines a normal valve condition or operation.

The reference transvalvular impedance representations present in the memory 160 can be pre-defined diastolic and systolic transvalvular impedance representations indicative of normal and correct valve function for the relevant heart valve. Alternatively and preferably, the reference diastolic and systolic transvalvular impedance representations have previously been determined by the IMD 100 to thereby get IMD- and patient-specific reference impedance representations. In such a case, the reference transvalvular impedance representations are basically determined in the same way as the diastolic and systolic transvalvular impedance representations, i.e. involving the operation of the signal generator 120, the impedance processor 130 and the representation processor 140 as previously described.

The reference transvalvular impedance representations are then preferably generated during a period of time when it is confirmed that no valve regurgitation, stenosis or other valve malfunction is present. This can be confirmed by the patient's physician, e.g. at a patient follow-up and/or IMD status check visit.

If the condition processor 150 concludes the presence of a tentative deleterious valve condition in at least one of the monitored heart valves, diagnostic data representative of the heart condition is generated. This data can be entered in the memory 160 for later uploading to an external communication unit. Alternatively, or in addition, the data can be directly and wirelessly sent to the external unit using the transmitter 170 and connected antenna 175 of the IMD 100. If the IMD 100 has an alarm unit capable of sounding an alarm signal or providing a tactile alarm signal, such unit could run an alarm if the condition processor 150 detects a severe deterioration of valve performance as determined based on an analysis of the diastolic and systolic transvalvular impedance representations.

This sorting of impedance data samples can be conducted solely based on the impedance data itself. In other words, the sorting of impedance data samples can be based on the change in transvalvular impedance values naturally occurs in diastole and systole. Thus, the respective well-known morphologies in the transvalvular impedance over a heart cycle are used to identify the start and end of diastole and systole.

In an alternative approach the IMD 100 comprises an electrogram or IEGM processor 190 for recording an intracardiac electrogram (IEGM) of the heart during the at least one heart cycle over which impedance data samples are determined. This IEGM processor 190 basically receives electric signals collected by its connected electrodes 312, 314, 322, 324, 324, preferably from the electrodes 312, 314, 322, 324 of the cardiac leads 310, 320 and originating from the heart. The sampling frequency of this IEGM data is preferably the same or has at least a well-defined relationship to the sampling frequency of the transvalvular impedance data. The diastolic and systolic phases of the heart cycle or cycles are typically identified from the IEGM data in a manner well known in the art. The start and end of diastole and systole are identified and impedance data samples coinciding with the start and end of diastole and systole are identified by the representation processor 140 using the predefined relationship between sampling frequencies.

The representation processor 140 can therefore sort the impedance data samples from the impedance processor 130 into diastolic and systolic transvalvular impedance data samples, respectively, based on the IEGM data from the IEGM processor 190.

As mentioned above, the respective impedance representation is preferably compared to a respective reference impedance representation. The resulting difference is compared to a threshold value and if exceeding the threshold value, the IMD 100 indicates that a negative heart valve condition has been determined. In such implementations, the condition processor 150 calculates the differences between the transvalvular impedance representations and the reference impedance representations:

$$\Delta Z_T^D = Z_T^D - RZ_T^D$$

$$\Delta Z_T^S = Z_T^S - RZ_T^S$$

where $Z_T^D$ denotes the diastolic transvalvular impedance representation, $Z_T^S$ denotes the systolic transvalvular impedance representation, $RZ_T^D$ denotes the reference diastolic transvalvular impedance representation, $RZ_T^S$ denotes the reference systolic transvalvular impedance representation and $\Delta Z_T^{D/S}$ represents the calculated differences in diastolic/systolic parameters.

The condition processor 150 compares these differences with respective threshold values, which may be the same or different, $T_D$, $T_S$. It is anticipated by the present invention that the same diastolic and systolic threshold values could be used regardless of which heart valve that is being monitored. In such a case, the threshold value could define a percentage value. Thus, a significant change is detected if the determined transvalvular impedance representation differs with more than the percentage value from the reference transvalvular impedance representation.

In an alternative implementation, each heart valve has its dedicated set of diastolic and systolic threshold values. This is expected to be a preferred implementation as the threshold values will typically be dependent on different factors, such as the particular patient, the impedance vectors used, the condition and implementation site of the electrodes, etc.

The actual threshold values can be set by the physician by analyzing transvalvular impedance data determined by the IMD for multiple different heart cycles. The physician can then identify a variance in the transvalvular representations that reflects normal fluctuations originating from the impedance measurements and may be due to different patient factors, such as body posture, heart rate, etc. Based on the analysis of such normal variations that are not due to any valve malfunction, the physician can set the thresholds to have desired values that will disregard normal variations but detect significant changes in the transvalvular impedance arising due to a valve malfunction.

In order to minimize the impact of different external factors on the impedance determination, such as body posture, patient activity level, etc., the IMD can be configured to perform the measurements once a set of such measurement conditions are met. For instance, the heart rate, as determined from the impedance data or the IEGM data, could be defined to be within an acceptable measurement interval. The posture of the patient can be determined using an implantable body posture sensor, which is well-known in the art. Alternatively, the IMD can be programmed to perform the impedance measurement at a time, when the patient is expected to be resting, such as during night.

In the following, the embodiments are disclosed further in connection with determination of particular valve conditions and for specific heart valves.

The present invention is based on the finding that a closed heart valve results in higher electric transvalvular impedance than an open valve. The reason for this is that the valve plane, including the valve tissue, has lower conductivity than myocardial tissue and blood. Thus, a closed valve will increase the impedance when measuring over the valve.

Stenosis of Mitral Valve, Tricuspid Valve

The mitral and tricuspid valves are positioned between the atriums and the ventricles in the heart, with the mitral valve between the left atrium and ventricle and the tricuspid valve between the right atrium and ventricle.

Figure 5A:
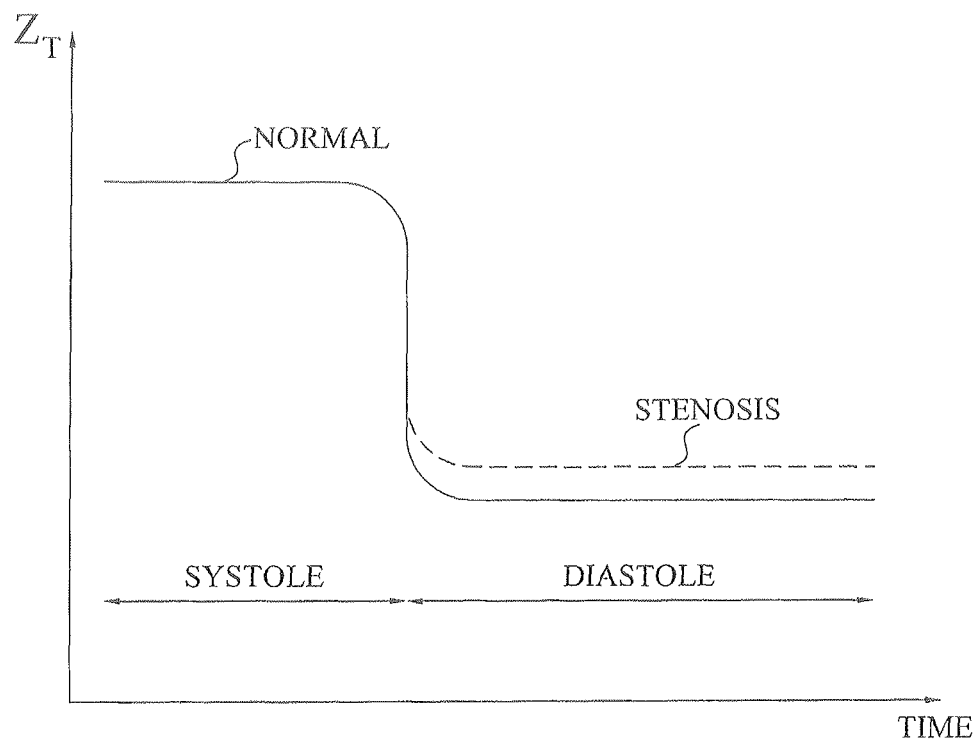
FIG. 5A is a diagram schematically illustrating a change in transvalvular impedances for the mitral valve and the tricuspid valve during valve stenosis.

FIG. 5A is a diagram illustrating the transvalvular impedance $Z_T$ determined according to an embodiment for the mitral valve or the tricuspid valve for a heart cycle. In the diagram, transvalvular impedance during normal valve condition is indicated by the unbroken line. As is seen in the figure, the transvalvular impedance for the mitral and tricuspid valves decreases significantly when going from systole, where the valves are closed, to diastole with the valves opened.

The condition processor 150 of the IMD 100 determines a tentative stenosis condition of the mitral and/or tricuspid valve if the difference between the diastolic transvalvular impedance representation and the reference diastolic transvalvular impedance representation exceeds the diastolic threshold value but the difference between the systolic transvalvular impedance representation and the reference systolic transvalvular impedance representation does not exceeds the systolic threshold value.

In other words the condition processor 150 determines the presence of mitral or tricuspid valve stenosis if: $\Delta Z_T^D = Z_T^D - RZ_T^D > T_D$ and $\Delta Z_T^S = Z_T^S - RZ_T^T \leq T_S$.

In mitral/tricuspid valve stenosis, the kinetics of the heart valve is impaired as the opening of the valve becomes impeded by the stenosis condition. Abnormal opening of the mitral/tricuspid valve during diastole when blood is to flow and be pumped from the left/right atrium to the ventricle will increase the transvalvular impedance as the valve cannot fully open correctly during diastole. This is indicated by the hatched line in FIG. 5A.

Mitral and tricuspid valve stenosis does not lead to any significant changes in systolic transvalvular impedance if the stenotic valve can be fully closed during systole.

Mitral Valve, Tricuspid Valve Regurgitation

The condition processor 150 of the IMD 100 determines a tentative regurgitation condition of the mitral and/or tricuspid valve if the difference between the systolic transvalvular impedance representation and the reference systolic transvalvular impedance representation exceeds the systolic threshold value but the difference between the diastolic transvalvular impedance representation and the reference diastolic transvalvular impedance representation does not exceed the diastolic threshold value.

In other words the condition processor 150 determines the presence of mitral or tricuspid valve regurgitation if: $\Delta Z_T^S = Z_T^S - RZ_T^S > T_S$ and $\Delta Z_T^D = Z_T^D - RZ_T^D \leq T_D$.

Figure 5B:
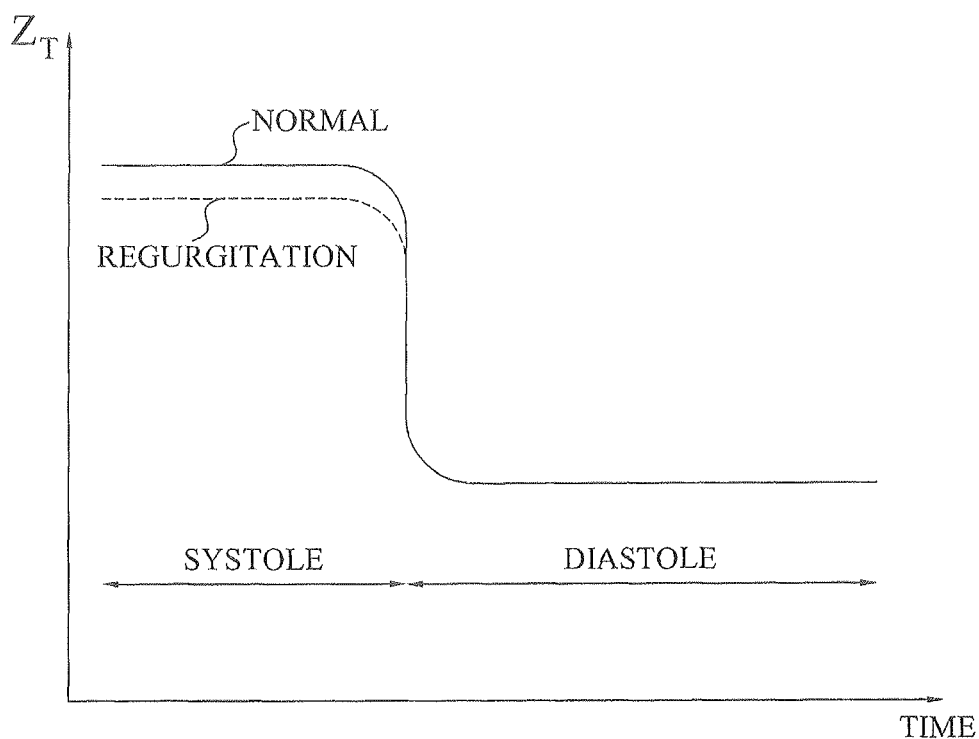
FIG. 5B is a diagram schematically illustrating a change in transvalvular impedances for the mitral valve and the tricuspid valve during valve regurgitation.

In mitral/tricuspid regurgitation the heart valve cannot fully close, thereby being partly open during systole. FIG. 5B is a diagram illustrating the change in mitral/tricuspid transvalvular impedance during normal valve operation, unbroken line, and during regurgitation, the hatched line. As the valve cannot fully close during systole, the conductivity over the valve increases and causing a significant reduction in the systolic part of the transvalvular impedance.

In clear contrast, the diastolic transvalvular impedance will not be or will only be marginally affected by the mitral/tricuspid valve regurgitation. This phenomenon is due to that the opening of the mitral/tricuspid valve is not significantly affected by the regurgitation condition, thereby at most only marginally affecting the diastolic portion of the transvalvular impedance.

Figure 7:
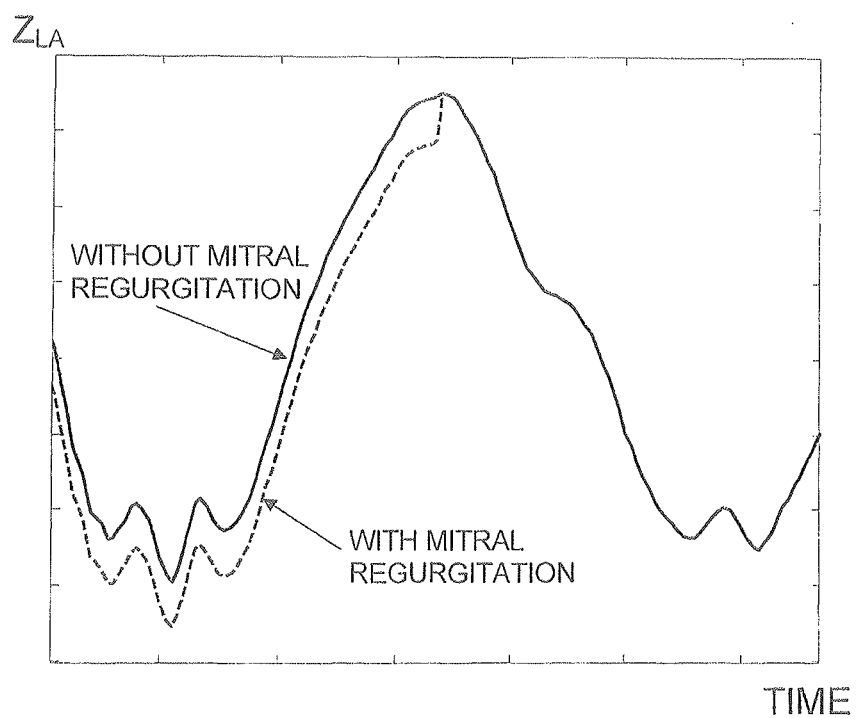
FIG. 7 is a diagram schematically illustrating a change in determined transvalvular impedance occurring during systole in the case of mitral valve regurgitation.

FIG. 7 illustrates the mitral transvalvular impedance recorded during a heart cycle. The unbroken line represents the transvalvular impedance without any heart valve malfunction. The hatched line indicates the transvalvular impedance for mitral valve regurgitation. The change in transvalvular impedance is mainly seen during systole, while the diastolic transvalvular impedance changes only marginally with mitral valve regurgitation.

Stenosis of Aortic Valve, Pulmonary Valve

The aortic and pulmonary valves are positioned between the ventricles and arteries connecting to ventricles and provided for transporting blood exiting the ventricles throughout the body, i.e. the systemic circulation system, or to the lungs, i.e. the pulmonary circulation system. The aortic valve is arranged between the left ventricle and the aorta, while the pulmonary valve is provided between the right ventricle and the pulmonary artery.

Figure 6A:
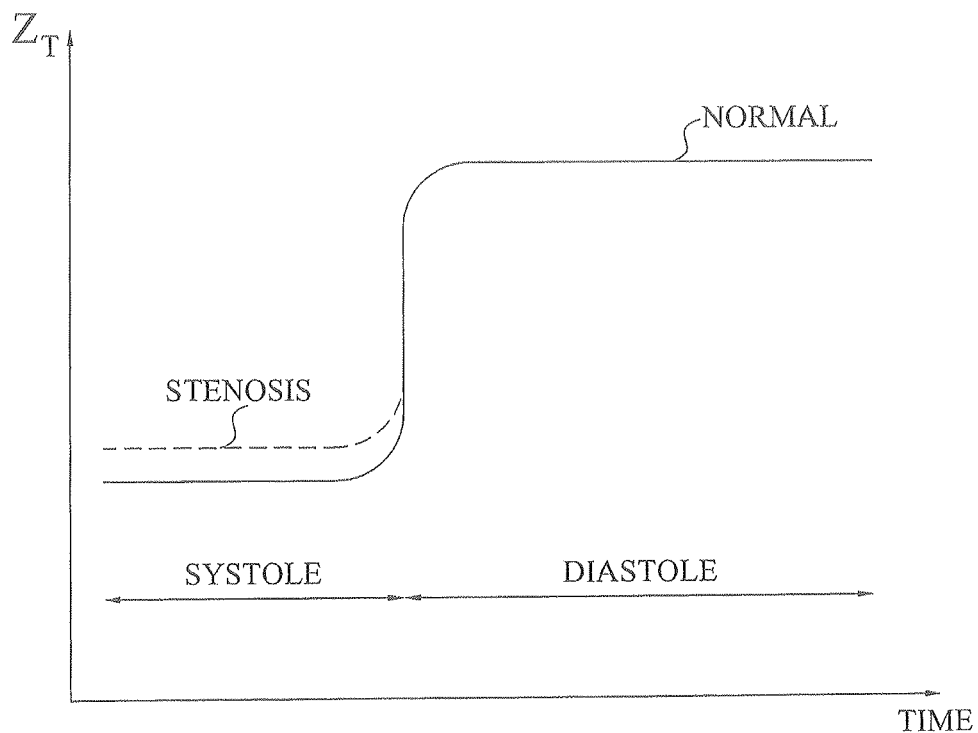
FIG. 6A is a diagram schematically illustrating a change in transvalvular impedances for the aortic valve and the pulmonary valve during valve stenosis.
Figure 6B:
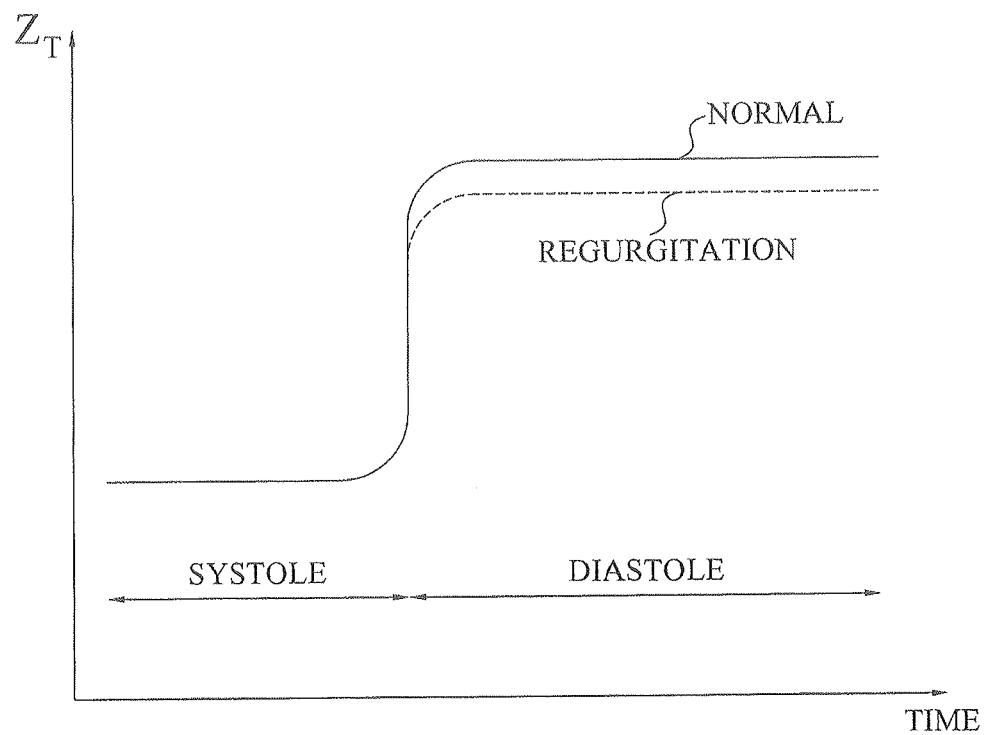
FIG. 6B is a diagram schematically illustrating a change in transvalvular impedances for the aortic valve and the pulmonary valve during valve regurgitation.

FIG. 6A is a diagram illustrating the transvalvular impedance $Z_T$ determined according to an embodiment for the aortic valve or the pulmonary valve for a heart cycle. In the diagram, transvalvular impedance during normal valve condition is indicated by the unbroken line. As is seen in the figure the transvalvular impedance for the aortic and pulmonary valves increases significantly when going from systole, where the valves are open, to diastole with the valves closed.

The condition processor 150 of the IMD 100 determines a tentative stenosis condition of the aortic and/or pulmonary valve if the difference between the systolic transvalvular impedance representation and the reference systolic transvalvular impedance representation exceeds the systolic threshold value but the difference between the diastolic transvalvular impedance representation and the reference diastolic transvalvular impedance representation does not exceed the diastolic threshold value.

In other words the condition processor 150 determines the presence of aortic or pulmonary valve regurgitation if: $\Delta Z_T^S = Z_T^S - RZ_T^S > T_S$ and $\Delta Z_T^D = Z_T^D - RZ_T^D \leq T_D$.

In aortic/pulmonary valve stenosis, the kinetics of the heart valve is impaired as the opening of the valve becomes impeded by the stenosis condition. Abnormal opening of the aortic/pulmonary valve during systole when blood is to flow and be pumped from the left/right ventricle to the connected artery will result in an increase in transvalvular impedance during systole.

It is expected that no significant change in the diastolic transvalvular impedance will be detectable during aortic/pulmonary valve stenosis if the valve can be fully closed during diastole.

Aortic Valve, Pulmonary Valve Regurgitation

The condition processor 150 of the IMD 100 determines a tentative regurgitation condition of the aortic and/or pulmonary valve if the difference between the diastolic transvalvular impedance representation and the reference diastolic transvalvular impedance representation exceeds the diastolic threshold value but the difference between the systolic transvalvular impedance representation and the reference systolic transvalvular impedance representation does not exceed the systolic threshold value.

In other words the condition processor 150 determines the presence of aortic or pulmonary valve regurgitation if: $\Delta Z_T^D = Z_T^D - RZ_T^D > T_D$ and $\Delta Z_T^S = Z_T^S - RZ_T^S \leq T_S$.

In aortic/pulmonary regurgitation the heart valve cannot fully close, thereby contributing to an increased conductivity over the valve plane during diastole and therefore a decrease in the diastolic transvalvular impedance.

In clear contrast, the systolic transvalvular impedance will not be or will only be marginally affected by the aortic/pulmonary valve regurgitation.

Different impedance vectors can generally be used depending on the particular heart valve that is to be monitored and the cardiac lead or leads connectable to the IMD. FIGS. 4A to 4F illustrates different such examples of impedance vectors that advantageously can be used in order to determine the transvalvular impedance data used herein for the valve condition determination.

FIG. 4A illustrates an electrode and lead setting that advantageously can be used when monitoring the mitral valve. In such a case, a right atrial lead 310 having at least one electrode 312, 314 is implanted in the right atrium 12 of the heart 10. A coronary vein lead or coronary sinus lead 330 having at least one electrode 332-338 is provided in connection with the left ventricle 18 of the heart. The mitral transvalvular impedance can be determined based on bipolar, tripolar or quadropolar measurements using one or two electrodes 312, 314 of the right atrial lead 310 and one or two electrodes 332-338 of the coronary vein lead 330. In bipolar measurements, one of the right atrial lead electrodes 312, 314 and one of the electrodes 332-338 of the coronary vein lead 330 are used for both applying the electric signal and for collecting the resulting electric signal. In tripolar measurement, one of the electrodes 312, 314, 332-338, either at the right atrial lead 310 or at the coronary vein lead 330, is used for both signal application and signal collection while remaining two electrodes are dedicated for signal application and signal collection, respectively. Quadropolar measurements, as is illustrated in FIG. 4A, uses a pair of signal applying electrodes 312, 332 on the two cardiac leads 310, 330 and another pair of signal collecting electrodes 314, 338 on the cardiac leads 310, 330.

The particular electrode setting illustrated in FIG. 4A, with the application of the electric signal over the electrodes 314, 338 and the collection of the resulting signal over the electrodes 312, 332 should merely be seen as an illustrative example. Actually any combination of at least two electrodes of the two cardiac leads 310, 330 can be used in bipolar, tripolar or quadropolar mitral transvalvular impedance measurements.

FIGS. 4B and 4C illustrate two possible electrode and lead arrangements that can be used for monitoring the aortic valve. Starting with FIG. 4B, the IMD 100 is in this case connected to a coronary vein lead or coronary sinus lead 330 having at least one electrode 332, 334. Bipolar or tripolar aortic transvalvular impedance measurements are available. In bipolar measurements, one of the electrodes 332, 334 of the lead 330 is used together with the case/can electrode 342 for both signal application and collection. With tripolar measurements, dedicated signal application electrode 334 and signal collection electrode 332 are used for the lead 330.

In FIG. 4C, the IMD 100 is further connected to a right atrial lead 310 having at least one electrode 312, 334. With a tripolar setting, the electric signal is applied between the case/can electrode 342 and one of the electrodes 334 of the coronary vein lead or coronary sinus lead 330 and the resulting electric signal is collected over the case/can electrode 342 and one of the electrodes 312 of the right atrial lead. Alternatively, the electric signal is applied between the can/case and the right atrial lead 310 and the resulting signal is collected between the can/case and the coronary vein lead 330.

It is expected that for most patients, the arrangement in FIG. 4B may be better isolate the aortic transvalvular contribution to the impedance data than the arrangement of FIG. 4C.

The tricuspid valve can be monitored by an electrode and lead configuration as is illustrated in FIG. 4D. Thus, a right atrial lead 310 is provided in the right atrium 12 and a right ventricular lead 320 is correspondingly provided in the right atrium 16 of the heart 10. As for the arrangement in FIG. 4A, bipolar, tripolar or quadropolar impedance measurements are available using one or two electrodes 312, 314 of the right atrial lead 310 and one or two electrodes 322, 324 of the right ventricular lead 320. The actual choice of impedance vector and signal applying and signal collecting electrodes is not that important as long as the electric signal is applied between an electrode 312, 314 in the right atrium and an electrode 322, 324 in the right ventricle and the resulting signal is correspondingly collected between electrode 312, 314 in the right atrium and an electrode 322, 324 in the right ventricle.

FIGS. 4E and 4F illustrate two possible arrangements that can be used for monitoring the pulmonary valve. In FIG. 4E the IMD 100 is connected to a right ventricular lead 320 having one or more electrodes 322, 324. Bipolar or tripolar impedance measurements are possible between the case/can electrode 342 and one or two electrodes 322, 324 in the right ventricle 16.

FIG. 4F illustrates an arrangement that allows tripolar or quadropolar pulmonary transvalvular impedance measurement. In addition to the right ventricular lead 320, the IMD 100 is also connected to a right atrial lead 310 having at least one electrode 312, 314. In tripolar measurements, the electric signal is applied between the case/can electrode 342 and a right ventricular electrode 322. The same right ventricular electrode 322 is used together with an electrode 312 of the right atrial lead 310 for collecting the resulting signal. Alternatively, signal application is performed between the right ventricular electrode 322 and the right atrial electrode 312, while signal collection involves the can/case electrode 342 and the right ventricular electrode 322.

With quadropolar measurements an electrode 332 of the right ventricular lead 320 is used together with one of the can/case electrode 342 or a right atrial electrode 312 for signal application and another right ventricular lead electrode 324 is used with the other of the can/case electrode 342 or a right atrial electrode 312 for signal collection.

The different lead configurations illustrated in FIGS. 4A to 4F may be combined depending on the heart valves that are to be monitored.

Today coronary vein leads are typically used instead of left ventricular leads introduced inside the left ventricle. It is currently within the medical field considered safer for the patient not to have any leads present in the left ventricle. However, disregarding any such potential risk, the teachings of the present invention can effectively be applied to a lead configuration where the coronary vein lead is replaced by a left ventricular lead.

In FIG. 4A, the coronary vein lead 330 has non-limitedly been illustrated by a so-called multi-electrode lead having a string of multiple, typically at least four electrodes 332-338 at different spatial positions along the lead 330. This is merely used for illustrating that the invention can be used in connection with such multi-electrode leads. Thus, any of the leads connectable to the IMD according to the arrangements in FIGS. 4A to 4F could be according to the multi-electrode type or according to a traditional lead type with one or, typically, two electrodes.

Different types of impedance representations can be determined by the representation processor 140 of the IMD 100 according to different embodiments. In a first embodiment, the respective diastolic and systolic transvalvular impedance waveforms are compared to reference diastolic and systolic transvalvular impedance waveforms or templates. The comparison can be made by calculating the difference between the determined waveform and the corresponding reference waveform in a sample-by-sample manner. The calculated differences are then added up to get an impedance parameter that is used by the condition processor 150 in determining the presence of any heart valve condition. The respective impedance parameters, one for diastole and one for systole, are compared to predefined threshold values that are either hardcoded in the IMD 100, such as present in the memory 160 or downloaded into the IMD 100 using a receiver 170 with connected antenna 175.

Alternatively, the representation processor 140 identifies pre-defined characteristics in the diastolic transvalvular impedance and the systolic transvalvular impedance. For instance, a global extreme transvalvular impedance value identified among the diastolic impedance samples and a corresponding global extreme value identified among the systolic impedance samples could be used as transvalvular impedance representations. In such a case, the global extreme value during diastole could be the minimum or maximum value among the diastolic transvalvular impedance samples. The systolic parameter is then the maximum or minimum value among the systolic transvalvular impedance samples.

The IMD 100 optionally has a quantification processor 180 that is arranged for calculating a quantification parameter from the diastolic and systolic transvalvular impedance representations. Such a quantification parameter may, for instance, be defined as the quotient between the above-mentioned minimum (or maximum) diastolic transvalvular impedance value and the maximum (or minimum) systolic transvalvular impedance value. The condition processor 150 then determines the current valve condition based on a comparison of the calculated quantification parameter from the quantification processor 180 and a previously determined or received reference quantification parameter. It is evident from the FIGS. 5A to 6B that the quotient between the minimum diastolic impedance value and the maximum systolic impedance value will be different in stenosis and regurgitation as compared to normal valve operation for the mitral and tricuspid valves. Correspondingly, the quotient between the maximum diastolic impedance value and the minimum systolic impedance value can be used for determining the presence of stenosis or regurgitation of the aortic or the pulmonary valve.

Alternatively, the representation processor 140 calculates one or more impedance characteristics or features from the diastolic and systolic transvalvular impedance data. A listing of different preferred impedance characteristics follows below. Any one or multiple of these characteristics can be used by embodiments:

Average impedance—the average impedance during diastole or systole;

Curvature length—the length of the impedance curve during diastole or systole;

Fractionation—is similar to the curvature length but amplitude normalization in the interval [0, 1] is used;

Systolic slope—identifies the maximum first time derivative in the transvalvular impedance signal during systole; and Peak to peak—takes the difference in the maximum and minimum transvalvular impedance value during diastole or systole.

Other impedance characteristics derivable from the diastolic transvalvular impedance data and the systolic transvalvular impedance data could be used instead of or as complement to the above-listed examples.

The calculated impedance characteristics during diastole or systole are compared to corresponding reference impedance characteristics calculated from a reference impedance waveform provided in the memory 160 of the IMD 100. In such a case, the reference impedance waveform is preferably an average waveform determined over multiple heart beats with no indication of any heart valve malfunction.

If the difference exceeds the predefined threshold a tentative heart valve malfunction may be present as described above.

A further possibility is to have the representation processor 140 to calculate the first time derivative of the diastolic and systolic transvalvular impedance. The first derivatives are plotted versus the respective regular transvalvular impedance data to form so-called impedance loops. Characteristics of the loops can be determined by the representation processor 140, such as loop area, loop radius, loop angle. Such characteristics can be calculated using the method described in U.S. Pat. No. 5,556,419, the teaching of which is hereby incorporated by reference. Alternatively, morphology comparisons using the calculated loops and corresponding reference loops determined from the reference diastolic and systolic impedance waveform as described in U.S. Pat. No. 5,427,112, the teaching of which is hereby incorporated by reference, can be used.

In an alternative implementation, the representation processor 140 comprises a baseline determiner 142 as is illustrated in FIG. 3. The baseline determiner 142 processes the transvalvular impedance data samples from the impedance processor and preferably average data samples determined from measurement over multiple heart cycles. Based on this processing, the baseline determiner 142 calculates a baseline transvalvular impedance value for the (average) heart cycle. A connected impedance converter 144 is implemented for superimposing the diastolic and systolic transvalvular impedance curves, for instance by flipping the diastolic part. This is conducted by inputting an impedance sample to a converting function:

$$Z_{T,i}^{C} = 2 \times Z_T^B - Z_{T,i}^{D/S}$$

where $Z_{T,i}^{D/S}$ transvalvular impedance data of sample i, $Z_T^B$ indicates the baseline transvalvular impedance determined by the baseline determiner 142 and $Z_{T,i}^{C}$ is the converted impedance data, flipped relative the baseline level. This converting is preferably performed for each impedance sample determined for the diastolic sub-phase of the (average) heart cycle or for each systolic impedance sample. Following the impedance conversion, both the diastolic and systolic transvalvular impedance samples can be superimposed and, for example, the representation processor 140 can calculate the difference between the diastolic and systolic transvalvular impedance samples. This difference is then used as impedance parameter and is compared by the condition processor with a reference impedance parameter.

The units 142 and 144 of the representation processor 140 may be implemented in hardware, software or combination of hardware and software. The units 142 and 144 may all be implemented in the representation processor 140. Alternatively, a distributed implementation is possible with at least one of the units 142 and 144 provided elsewhere in the IMD.

The actual value or values of the thresholds that are used according to the embodiments can be hardcoded in the IMD at the time of implantation. Alternatively, they are downloaded by the physician following the implantation time, such as at a patient follow-up meeting. The threshold values may be fixed or can be updated, for instance by the physician by downloading new, updated threshold values. This may, for instance, be considered if the IMD has notified that there is a valve malfunction based on the determined impedance data. The physician can then, once he/she has concluded that the IMD has determined such a valve malfunction, perform a more complete investigation of the valve condition, such as using an ultrasound probe. If the physician determines that no valve malfunction is present even though the IMD signals this, it might be due to that the local environment around the signal applying and signal measuring electrodes of the cardiac leads has changed somewhat, such as through the ingrowth of connective tissue. Such a change in local environment will in turn be captured in the transvalvular impedance data and will affect the determined transvalvular impedance representations. The physician can therefore update threshold values to compensate for this change in electrode environment.

In an alternative and typically more preferred approach, the IMD itself, possibly following that the physician has concluded that no valve malfunction is present, updates the reference transvalvular impedance representations based on the latest transvalvular impedance representations. The reference transvalvular impedance representation can, for example, be in the form of an average of several different transvalvular impedance representations determined at different time instances. A weighted average is typically preferred to thereby more heavily weight a more recently determined impedance representation as compared to an outdated impedance representation.

The units 110 to 190 of the IMD 100 can be implemented in hardware, software of a combination of hardware and software.

In the foregoing, the IMD has been described as containing the processing functionalities required for determining the transvalvular impedance data, estimating the diastolic and systolic transvalvular impedance representations and performing the valve condition determination. FIG. 1 illustrates a system 300 including the IMD 100 and a non-implantable communication and processing device 200, exemplified as the programmer or physician's workstation in FIG. 1. The system 300 includes the previously described impedance processor 230, the representation processor 240 and the condition processor 250. In a first embodiment all these processors are provided in the IMD 100 as illustrated in FIG. 2. The IMD 100 may then communicate the result of the valve condition determination to the receiver 270 of the programmer 200, for instance for display to the physician on the display screen 210.

A second embodiment of the system 300 has the impedance processor and the representation processor arranged in the IMD 100. However, the condition processor 250 is instead arranged in the programmer 200. The IMD 100 therefore determines the diastolic and systolic transvalvular impedance representations and transmits them to the receiver 270 of the programmer 200. The condition processor 250 uses these transvalvular impedance representations for determining the condition of a heart valve as previously described.

In a third embodiment of the system 300, the impedance processor is implemented in the IMD 100, while both the representation processor 240 and the condition processor 250 are arranged in the programmer 200. The impedance data determined by the impedance processor is therefore uploaded to the receiver 270 of the programmer 200 for being input to the representation processor 240.

Finally, a fourth embodiment of the system 300 has the impedance processor 230, representation processor 240 and the condition processor 250 implemented in the programmer 200. The IMD 100 therefore merely collects the raw electric signal and transmits the relevant voltage and current data to the programmer 200 for calculation of the impedance data in the impedance processor 230.

Thus, the processors can be implemented in the IMD 100 or in a non-implantable communication and processing device 200. The operation of the processors is basically the same regardless of implementation site. Correspondingly, the quantization processor of FIG. 2 may instead be provided in the programmer 200 in particular if the condition processor 250 is found in the programmer 200. Correspondingly, the IEGM processor may be found in the programmer 200, especially if the representation processor 240 and the condition processor 250 are arranged in the programmer 200.

The programmer 200 may also contain data memory in similarity to the IMD 100.

If the majority of the processors are provided in the IMD, more of the data processing is of course performed in the IMD. However, the amount of data sent to the programmer can be kept fairly small, i.e. merely indicating that a heart valve malfunction has been detected, which valve that has been effected (can be managed by a 2-bit valve identifier) and possibly what type of malfunction that has been detected (can be managed by a 2-bit condition identifier in the case of normal, stenosis and regurgitation condition). If the processors instead are provided in the non-implantable device, the processing of the data is performed therein. The IMD must then, though, transmit fairly large amount of raw data to be used by the processors.

Figure 9:
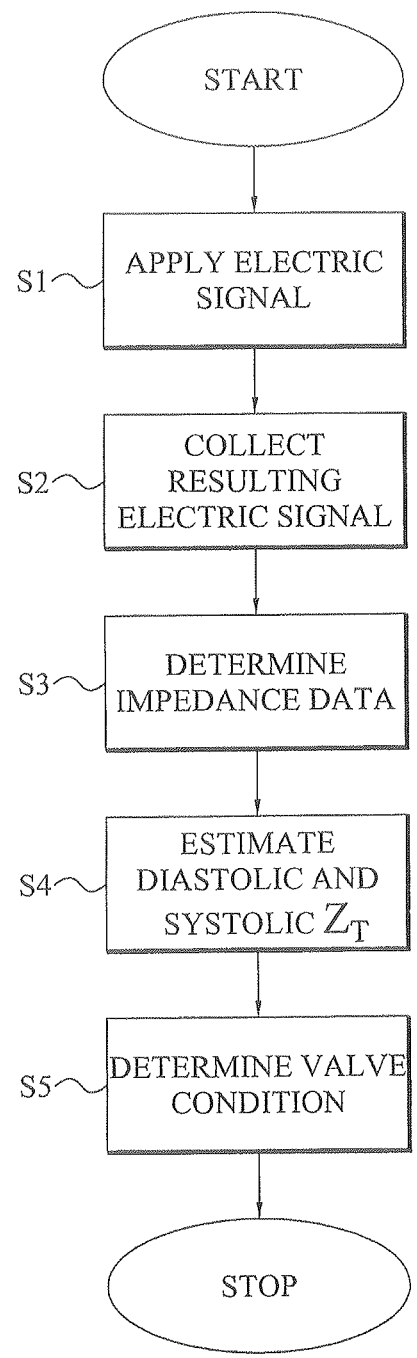
FIG. 9 is a flow diagram illustrating a method of determining a condition of a heart valve.

FIG. 9 is a flow diagram illustrating a method of determining a condition of a valve of a heart in a subject, preferably human subject. The method starts with the steps S1 and S2. Step S1 applies an electric signal, AC signal, over at least a portion of the heart during at least one heart cycle. A resulting electric signal, AC signal, is collected over at least a portion of the heart in step S2. Step S3 determines impedance data based on the applied electric signal, such as based on the current of the of the electric signal, and based on the collected resulting electric signal, such as based on the voltage of the resulting electric signal. This impedance data are furthermore reflective of the transvalvular impedance of a heart valve during at least one heart cycle.

The impedance data are preferably determined based on measurements conducted during multiple successive or non-successive heart cycles to thereby obtain average impedance data. This in turn reduces the effect of noise and other disturbances that otherwise may have an impact if the measurements are limited to a single heart cycle. Generally, an average over 5-10 heart cycles often works really well in terms of noise suppression.

A next step S4 estimates a diastolic transvalvular impedance representation and a systolic transvalvular impedance representation based on the impedance data determined in step S3.

The condition of one or more heart valves is determined in step S5 for the purpose of detecting any valve malfunction or confirming normal valve condition. The condition determination is furthermore conducted based on the diastolic and systolic transvalvular impedance representations from step S4

Steps S1 and S2 are conducted by the IMD. The steps S3 to S5 may be performed in the IMD or may be performed by the programmer.

The procedure illustrated by steps S1 to S5 of FIG. 9 may be conducted once, such as upon a triggering signal generated by the IMD itself or received from an external communication unit, such as programmer. Alternatively, the method is performed periodically or intermittently according to a defined monitoring schedule. Thus, the method can be repeated once per day, once per week, once per month or with some other periodicity.

The transvalvular impedance representations can, as has been previously discussed, average transvalvular impedance values determined based on the diastolic and systolic impedance data samples for multiple heart cycles. For instance, the global extreme values in the diastolic and systolic impedance data can be identified and used for calculating a quantification parameter as is illustrated in step S20 of FIG. 11. The quantification parameter is then compared to a reference quantification parameter in step S5 of FIG. 9 for the purpose of confirming normal valve function or determining a valve malfunction.

FIG. 10 is a flow diagram illustrating another embodiment of estimating impedance representations. The method continues from step S3 of FIG. 9. A next step S10 determines a baseline transvalvular impedance value for (average) heart cycle. This baseline transvalvular impedance value is used in step S11 for converting the diastolic or the systolic transvalvular impedance data sample to flipped values relative the baseline level. The method then continues to step S5 of FIG. 9, where the converted diastolic (or systolic) transvalvular impedance values are compared to the systolic (or diastolic) transvalvular impedance values for the purpose of determining a quantification parameter as discussed above in connection with step S20 of FIG. 11.

FIG. 12 is a flow diagram illustrating additional steps of the determining method in FIG. 9. The method continues from step S3 of FIG. 9. A next step S30 records an IEGM of the heart, preferably in parallel with the signal measurements used as a basis for determining the transvalvular impedance data. The IEGM is used in step S31 for sorting and classifying the impedance data samples into impedance data samples relating to diastole of the heart cycle, the multiple heart cycles or the average heart cycle and those data samples that coincide with systole. The method then continues to step S4, where the diastolic and systolic transvalvular impedance representations are determined based on the sorted impedance data samples.

The valve condition data generated by embodiments is not necessarily limited to usage as highly valuable diagnostic information to detect any valve condition or any other medical condition that causes symptoms of valve malfunction. IMD implemented for providing cardiac resynchronization therapy (CRT) to patients having dyssynchrony between the left and right ventricles can benefit from the embodiments. When optimizing the CRT parameters of the IMD, valve regurgitation, in particular mitral valve regurgitation, may occur in the case on non-optimal CRT parameters. The valve condition monitoring of the embodiments can therefore be used as a complement during CRT parameter adjustment, in particular AV time and VV time, optimization by detecting the parameter settings that minimizes or leads to no mitral valve regurgitation.

Although modifications and changes may be suggested by those skilled in the art, it is the intention of the inventors to embody within the patent warranted heron all changes and modifications as reasonably and properly come within the scope of their contribution to the art.

What is claims is:

1. A method of determining a condition of a valve of a heart in a subject, said method comprising:
  applying an electric signal over a portion of said heart during at least one heart cycle;
  in computerized processing circuitry, determining, based on said electric signal and a resulting electric signal measured over said portion of said heart, impedance data reflective of a transvalvular impedance of said valve during said at least one heart cycle;
  in computerized processing circuitry, estimating a diastolic transvalvular impedance representation and a systolic transvalvular impedance representation based on said impedance data; and in computerized processing circuitry, determining said condition of said valve based on said diastolic transvalvular impedance representation and said systolic transvalvular impedance representation, and emitting, in electronic form, an indication of said condition of said valve from said computerized processing circuitry.

2. The method according to claim 1, wherein said estimating comprises estimating a diastolic average transvalvular impedance value and a systolic average transvalvular impedance value based on said impedance data.

3. The method according to claim 1, wherein said estimating comprises estimating a minimum transvalvular impedance value for a diastolic phase of said at least one heart cycle and a maximum transvalvular impedance value for a systolic phase of said at least one heart cycle based on said impedance data.

4. The method according to claim 1, wherein said estimating comprises:
determining a baseline transvalvular impedance value for said at least one heart cycle based on said impedance data; and
converting impedance data corresponding to one of a diastolic phase and a systolic phase of said impedance data according to
$$Z_{T,i}^{C} = 2 \times Z_{T}^{B} - Z_{T,i}^{D/S},$$
where $Z_{T,i}^{C}$ denotes converted impedance data of data sample i,
$Z_{T}^{B}$ denotes said baseline transvalvular impedance value and
$Z_{T,i}^{D/S}$ denotes impedance data of sample i.

5. The method according to claim 1, further comprising in computerized processing circuitry, determining, based on said diastolic transvalvular impedance representation and said systolic transvalvular impedance representation, a quantification parameter representative of a relation between said diastolic transvalvular impedance representation and said systolic transvalvular impedance representation, and wherein said determining said condition comprises determining said condition of said valve based on said quantification parameter and a reference quantification parameter.

6. The method according to claim 1, wherein said valve located between an atrium of a first side of said heart and a ventricle of said first side of said heart and wherein said determining comprises determining a regurgitation condition of said valve if a difference between said systolic transvalvular impedance representation and a systolic reference representation exceeds a systolic threshold but a difference between said diastolic transvalvular impedance representation and a diastolic reference representation does not exceed a diastolic threshold.

7. The method according to claim 1, wherein said valve is located between an atrium of a first side of said heart and a ventricle of said first side of said heart and wherein said determining comprises determining a stenosis condition of said valve if a difference between said diastolic transvalvular impedance representation and a diastolic reference representation exceeds a diastolic threshold but a difference between said systolic transvalvular impedance representation and a systolic reference representation does not exceed a systolic threshold.

8. The method according to claim 1, wherein said valve is located between a ventricle of said heart and an artery connected to said ventricle and said determining comprises determining a regurgitation condition of said valve if a difference between said diastolic transvalvular impedance representation and a diastolic reference representation exceeds a diastolic threshold but a difference between said systolic transvalvular impedance representation and a systolic reference representation does not exceed a systolic threshold.

9. The method according to claim 1, wherein said valve is located between a ventricle of said heart and an artery connected to said ventricle and wherein said determining comprises determining a stenosis condition of said valve if a difference between said systolic transvalvular impedance representation and a systolic reference representation exceeds a systolic threshold but a difference between said diastolic transvalvular impedance representation and a diastolic reference representation does not exceed a systolic threshold.

10. The method according to claim 1, further comprising:
recording an intracardiac electrogram of said heart over said at least one heart cycle; and
in computerized processing circuitry, identifying, based on said intracardiac electrogram, data samples of said impedance data comprising diastolic impedance data and data samples of said impedance data comprising systolic atrial impedance data.

* * * * *